(12) United States Patent
Hosoi et al.

(10) Patent No.: US 9,132,108 B2
(45) Date of Patent: Sep. 15, 2015

(54) PHARMACEUTICAL COMPOSITION FOR AMELIORATING AND/OR PREVENTING LEPTIN RESISTANCE, AND USE THEREOF

(75) Inventors: Toru Hosoi, Hiroshima (JP); Koichiro Ozawa, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 1003 days.

(21) Appl. No.: 13/263,966

(22) PCT Filed: Apr. 14, 2010

(86) PCT No.: PCT/JP2010/002691
§ 371 (c)(1),
(2), (4) Date: Oct. 11, 2011

(87) PCT Pub. No.: WO2010/119674
PCT Pub. Date: Oct. 21, 2010

(65) Prior Publication Data
US 2012/0041228 A1 Feb. 16, 2012

(30) Foreign Application Priority Data

Apr. 17, 2009 (JP) ................................. 2009-100894
Nov. 2, 2009 (JP) ................................. 2009-251958

(51) Int. Cl.
| | | |
|---|---|---|
| *A61K 31/192* | (2006.01) | |
| *A61P 3/04* | (2006.01) | |
| *A61P 3/06* | (2006.01) | |
| *A61P 3/10* | (2006.01) | |
| *A61P 9/10* | (2006.01) | |
| *A61P 9/12* | (2006.01) | |

(52) U.S. Cl.
CPC .................................... *A61K 31/192* (2013.01)

(58) Field of Classification Search
CPC ............................. C07C 57/58; A61K 31/192
See application file for complete search history.

(56) References Cited

U.S. PATENT DOCUMENTS

| 4,439,451 A * | 3/1984 | Coleman ........................ 514/570 |
| 2004/0204472 A1 | 10/2004 | Briggs et al. |
| 2008/0233053 A1 * | 9/2008 | Gross et al. ....................... 424/45 |

FOREIGN PATENT DOCUMENTS

JP 2008-208091 A 9/2008

OTHER PUBLICATIONS

Martin, S. S. et al. "Leptin Resistance. A Possible Interface of Inflammation and Metabolism in Obesity-Related Cardiovascular Disease" J. Am. Coll. Cardiol. 2008, 52, 1201-10.*

Pyrko et al. "Calcium-activated endoplasmic reticulum stress as a major component of tumor cell death induced by 2,5-dimethyl-celecoxib, a non-coxib analogue of celecoxib." Mol. Cancer. Ther. 2007, 6(4), 1262-1275.*
Banks et al. "Triglycerides induce leptin resistance at the blood-brain barrier" Diabetes 2004, 53, 1253-1260.*
Munzberg, Heike, et al., "Molecular and anatomical determinants of central leptin resistance," Nature Neuroscience, May 2005, vol. 8, No. 5: pp. 566-570.
Bence, Kendra K., et al., "Neuronal PTP1B regulates body weight, adiposity and leptin action," Nature Medicine, Aug. 2006, vol. 12, No. 8: pp. 917-924.
Bjorbaek, Christian, et al., "Identification of SOCS-3 as a Potential Mediator of Central Leptin Resistance," Molecular Cell, Mar. 1998, vol. 1: pp. 619-625.
Bjorbaek, Christian, "The role of SOCS-3 in Leptin Signaling and Leptin Resistance," The Journal of Biological Chemistry, Oct. 15, 1999, vol. 274(42): pp. 30059-30065.
Van Heek, Margaret, et al., "Diet-induced Obese Mice Develop Peripheral, but Not Central, Resistance to Leptin," J. Clin. Invest., Feb. 1997, vol. 99(3): pp. 385-390.
Cheng, Alan, et al., "Attenuation of Leptin Action and Regulation of Obesity by Protein Tyrosine Phosphatase 1B,"Development Cell, Apr. 2002, vol. 2: pp. 497-503.
Zabolotny, Janice M., et al., "PTP1B Regulates Leptin Signal Transduction in Vivo," Developmental Cell, Apr. 2002, vol. 2: pp. 489-495.
"Success in labeling drugs having antipyretic and analgesic actions to be visible in vivo—Observing behavior of anti-inflammatory drug in vivo by PET molecular imaging"—http://www.riken.go.jp/r-world/research/results/2010/100309/index.html, Mar. 9, 2010 (partial translation).
Lee, Gwo-Hwa, et al., "Abnormal splicing of the leptin receptor in diabetic mice," Nature, Feb. 15, 1996, vol. 379: pp. 632-635.
Chen, Hong, et al., "Evidence That the Diabetes Gene Encodes the Leptin Receptor: Identification of a Mutation in the Leptin Receptor Gene in db/db Mice," Cell, Feb. 9, 1996, vol. 84: pp. 491-495.
Hosoi, Toru, et al., "Endoplasmic Reticulum Stress Induces Leptin Resistance," Molecular Pharmacology, 2008, vol. 74, No. 6: pp. 1610-1619.
Ozcan, Lale, et al., "Endoplasmic Reticulum Stress Plays a Central Role in Development of Leptin Resistance," Cell Matabolism, Jan. 7, 2009, vol. 9: pp. 35-51.
Office Action of corresponding JP Patent Application No. 2011-509214 dated Apr. 8, 2014 (full English translation attached).
Kadota, I., et al., "Effect of Long-term Administration of . . . ", Jpn. Arch. Int. Med., vol. 29, No. 3, Mar. 30, 1982, pp. 131-143 (English abstract included).
Office Action of corresponding JP Patent Application No. 2011-509214 dated Nov. 4, 2014 (English translation provided).
Ota, Tsuguhito, "Examination on significance of ER stress in hypercholesterolemia and formation of fatty liver," Bunshi Shokaki Byo (Molecular Gastrointestinal Medicine), vol. 6, No. 1, 2009, pp. 35-40 (partial English translation provided).

* cited by examiner

*Primary Examiner* — Joseph Kosack
*Assistant Examiner* — Amanda L Aguirre
(74) *Attorney, Agent, or Firm* — Casimir Jones, S.C.

(57) ABSTRACT

The present invention provides a pharmaceutical composition for ameliorating and/or preventing leptin resistance. The pharmaceutical composition of the present invention contains flurbiprofen.

2 Claims, 10 Drawing Sheets

(a) Before Fasting (b) After Fasting

PHARMACEUTICAL COMPOSITION FOR AMELIORATING AND/OR PREVENTING LEPTIN RESISTANCE, AND USE THEREOF

TECHNICAL FIELD

The present invention relates to a pharmaceutical composition for ameliorating and/or preventing leptin resistance, and use thereof.

BACKGROUND ART

Leptin is a hormone secreted mainly by fatty tissue. When leptin is secreted into circulating blood, leptin subdues food intake or promotes energy expenditure via leptin receptors in a hypothalamus and a brain stem, thereby reducing body weight.

Recently, there has been reported so-called "leptin resistance" which means decrease in the function of leptin in spite of increase in circulating leptin levels (see Non-patent Literature 1).

There have been conceived many causes as a mechanism behind acquisition of leptin resistance. For example, Non-patent Literatures 2, 6, and 7 describe that protein tyrosine phosphatase 1B contributes to leptin resistance.

Further, Non-patent Literatures 3 and 4 describe that increased expression of suppressor of cytokine signaling 3 (SOCS3) induces leptin resistance. Further, Non-patent Literature 5 suggests that some causes of induction of leptin resistance would be due to a failure of a system which transports circulating leptin to a central nervous system, i.e. blood-brain barrier, rather than reactivity of leptin itself.

Recently, it has been conceived that leptin resistance is a cause for diabetes, hypertension, hyperlipemia, arteriosclerosis etc. Ameliorating and/or preventing leptin resistance is important also for ameliorating and/or preventing diseases resulting from leptin resistance.

For example, Patent Literature 1 discloses a pharmaceutical composition for ameliorating endoplasmic reticulum stress in central nerve. Such a pharmaceutical composition is characterized by containing a nonsteroidal anti-inflammatory compound. Patent Literature 1 suggests that flurbiprofen is usable as the nonsteroidal anti-inflammatory compound.

CITATION LIST

Patent Literatures

[Patent Literature 1]
Japanese Patent Application Publication No. 2008-208091 (published on Sep. 11, 2008)

Non-Patent Literatures

[Non-Patent Literature 1]
H. Munzberg, M. G. Myers, Jr., Molecular and anatomical determinants of central leptin resistance. Nature Neuroscience, 2005, 8: 566-570.

[Non-Patent Literature 2]
Bence K K, Delibegovic M, Xue B, Gorgun C Z, Hotamisligil G S, Neel B G, and Kahn B B (2006) Neuronal PTP1B regulates body weight, adiposity and leptin action. Nature Med 12: 917-924.

[Non-Patent Literature 3]
C. Bjorbaek, J. K. Elmquist, J. D. Frantz, S. E. Shoelson, J. S. Flier, Identification of SOCS-3 as a Potential Mediator of Central Leptin Resistance. Molecular Cell, 1998, 1: 619-625.

[Non-Patent Literature 4]
C. Bjorbaek, K. El-Haschimi, J. D. Frantz, J. S. Flier, The Role of SOCS-3 in Leptin Signaling and Leptin Resistance. THE JOURNAL OF BIOLOGICAL CHEMISTRY, 1999, 274(42): 30059-30065.

[Non-Patent Literature 5]
M. V. Heek, D. S. Compton, C. F. France, R. P. Tedesco, A. B. Fawzi, M. P. Graziano, E. J. Sybertz, C. D. Strader, H. R. Davis, Jr., Diet-induced Obese Mice Develop Peripheral, but Not Central, Resistance to Leptin. J. Clin. Invest., 1997, 99(3): 385-390.

[Non-Patent Literature 6]
Cheng A, Uetani N, Simoncic P D, Chaubey V P, Lee-Loy A, McGlade C J, Kennedy B P, and Tremblay M L (2002) Attenuation of leptin action and regulation of obesity by protein tyrosine phosphatase 1B. Dev Cell 2: 497-503.

[Non-Patent Literature 7]
Zabolotny J M, Bence-Hanulec K K, Stricker-Krongrad A, Haj F, Wang Y, Minokoshi Y, Kim Y B, Elmquist J K, Tartaglia L A, Kahn B B, et al. (2002) PTP1B regulates leptin signal transduction in vivo. Dev Cell 2: 489-495.

SUMMARY OF INVENTION

Technical Problem

However, the pharmaceutical composition disclosed in Patent Literature 1 is intended for ameliorating endoplasmic reticulum stress in central nerve. No pharmaceutical composition has been developed so far in consideration of ameliorating and/or preventing leptin resistance.

As described above, leptin resistance is induced by various causes, and a fundamental mechanism of leptin resistance has not yet been found. Consequently, a conclusive therapeutic agent for ameliorating and/or preventing leptin resistance has not yet been found.

The present invention was made in view of the foregoing problems. An object of the present invention is to provide a pharmaceutical composition for ameliorating and/or preventing leptin resistance, and use thereof.

Solution to Problem

The inventors of the present invention have diligently studied the above objects and found that flurbiprofen, which has been used as a nonsteroidal anti-inflammatory agent for diseases such as chronic rheumatism and coxalgia, is effective for ameliorating and/or preventing leptin resistance, and thus completed the present invention.

So far, it has not been known at all that flurbiprofen is effective for ameliorating and/or preventing leptin resistance. Accordingly, the inventors of the present invention are the first persons to find and disclose that flurbiprofen is effective for ameliorating and/or preventing leptin resistance.

A pharmaceutical composition of the present invention for ameliorating and/or preventing leptin resistance contains flurbiprofen.

The present invention encompasses use of flurbiprofen in producing a pharmaceutical composition for ameliorating and/or preventing leptin resistance.

Patent Literature 1 describes that expression of GRP78 and CHOP induced by endoplasmic reticulum stress is prevented by flurbiprofen. This only suggests that flurbiprofen is usable for ameliorating endoplasmic reticulum stress. As described above, leptin resistance is also induced by causes other than endoplasmic reticulum stress. Therefore, although Patent Literature 1 suggests that flurbiprofen is effective for ameliorating endoplasmic reticulum stress which is a cause for acquisition of leptin resistance, Patent Literature 1 would not enable a person skilled in the art to expect that flurbiprofen is effective for ameliorating leptin resistance. Accordingly, a person skilled in the art could not conceive the present invention based on Patent Literature 1 etc.

For a fuller understanding of other objects, the nature and advantages of the invention, reference should be made to the ensuing detailed description taken in conjunction with the accompanying drawings.

Advantageous Effects of Invention

The pharmaceutical composition of the present invention has a very excellent effect of ameliorating and/or preventing leptin resistance.

Flurbiprofen contained in the pharmaceutical composition of the present invention has been already placed on the market as a non-steroidal anti-inflammatory agent. Accordingly, the information regarding side-effects derived from administration of flurbiprofen (such as stomach discomfort, anorexia, and nausea) can be known before use. Further, it has been confirmed that no dependence on flurbiprofen or no development of resistance to flurbiprofen is observed. Therefore, flurbiprofen would be used quite excellently as a long-term administrable and safe medicament for ameliorating and/or preventing leptin resistance.

DESCRIPTION OF EMBODIMENTS

Figure 1:
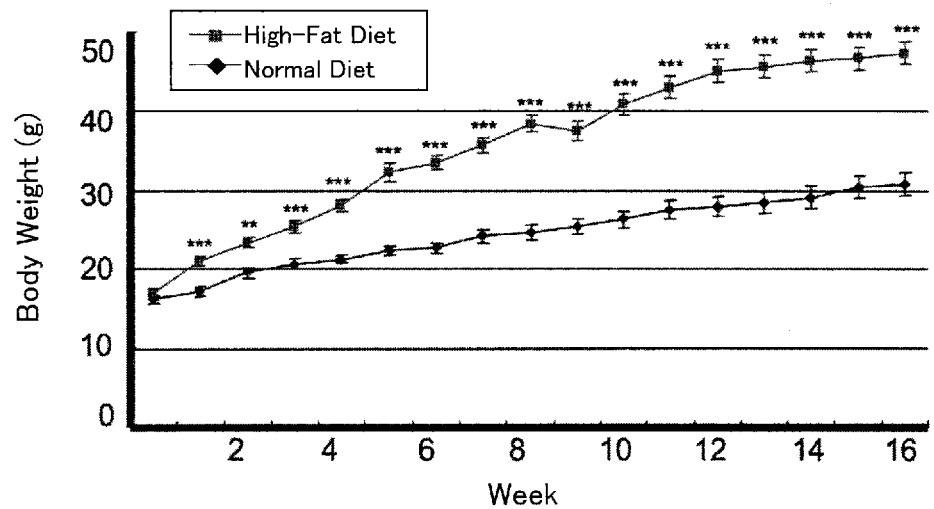
FIG. 1 is a graph showing changes in body weights of mice which had been given high-fat diet or normal diet.

The following explains an embodiment of the present invention. It should be noted that the present invention is not limited to the following embodiment, and may encompass many variations and modifications within the scope of the descriptions. Further, all the academic literatures and patent literatures cited in the specification are incorporated herein by reference. In the specification, the expression "A-B" indicates "not less than A and not more than B" unless otherwise stated.

[Pharmaceutical Composition]

A pharmaceutical composition of the present invention is a pharmaceutical composition for ameliorating and/or preventing leptin resistance and contains flurbiprofen. In the specification, "flurbiprofen" includes a composition (I) represented by a general formula below and enantiomers thereof, and pharmaceutically acceptable salts thereof.

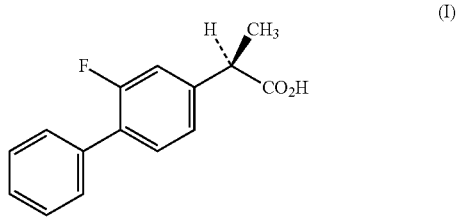

(I)

Further, in the specification, "flurbiprofen" includes derivatives having a structure of the composition (I).

The "derivatives" may be a one which exhibits, in the form of a derivative, activity similar to that of the composition (I). Alternatively, the "derivatives" may be a so-called "prodrug" which is inactive in the form of a derivative but is reactivated when it is converted into the composition (I) under physiological conditions in vivo by e.g. enzymic reaction. Examples of such "derivatives" include: derivatives which are the composition (I) with esterified carboxylic acid; and derivatives which are the composition (I) with axetilified carboxylic acid.

Examples of the derivatives which are the composition (I) with esterified carboxylic acid include derivatives which are the composition (I) with methylesterified carboxylic acid, ethylesterified carboxylic acid, and phenylesterified carboxylic acid.

Among them, derivatives which are the composition (I) with methylesterified carboxylic acid are reported to have improved transferability to brain compared with the composition (I) (http://www.riken.go.jp/r-world/research/results/

2010/100309/index.html) (retrieved on Apr. 5, 2010). These "derivatives" can be produced from the composition (I) by a conventional and publicly known method.

The pharmaceutical composition of the present invention can be produced by a method publicly known in the field of medicine manufacture. The content of flurbiprofen in the pharmaceutical composition of the present invention is not particularly limited as long as (i) the content is determined in consideration of the form of the pharmaceutical composition, the method of administration, the purpose of use, and age, body weight, symptom etc. of the subject of administration (patient) and (ii) the use of the pharmaceutical composition can administer flurbiprofen in a later-mentioned range. The lower limit of the administration amount of flurbiprofen is preferably 0.013-401 mg/kg, more preferably 0.13-40 mg/kg, and further more preferably 0.44-12 mg/kg per day for an adult (with body weight of 60 kg).

However, the range of the preferable administration amount varies according to various conditions. There is a case where an amount smaller than the above administration amount is sufficient, or there is a case where an amount larger than the above administration amount is necessary.

The following explains the "leptin resistance". In the specification, the "leptin resistance" means a state where leptin is present in blood but a leptin's signal in a hypothalamus is prevented.

The "leptin's signal" is explained briefly below. Leptin acts on a leptin receptor belonging to the family of cytokine receptors and activates Jak2. Consequently, STAT3 which is a transcriptional factor is phosphorylated. The phosphorylated STAT3 moves into a nucleus and activates transcription of proopiomelano-cortin (POMC) etc. (H. Munzberg, M. G. Myers, Jr., Molecular and anatomical determinants of central leptin resistance. Nature Neuroscience, 2005, 8: 566-570). Accordingly, it is possible to confirm whether a leptin's signal is prevented or not by analyzing whether STAT3 in a tissue where a leptin receptor is expressed is phosphorylated or not after leptin administration.

Therefore, in the specification, the term "prevention of leptin resistance" means to cause the STAT3 phosphorylation by leptin in a hypothalamus to be maintained, for example, even under conditions where leptin resistance is induced (e.g. as will be mentioned later, high-fat diet is given for a long time). Further, the term "amelioration of leptin resistance" means that STAT3 gets phosphorylated again from a state where STAT3 phosphorylation by leptin in a hypothalamus is prevented by induction of leptin resistance.

As described in later-mentioned Examples, "prevention of leptin resistance" or "amelioration of leptin resistance" can be evaluated with body weight, blood glucose level, and circulating leptin levels as well as STAT3 phosphorylation as indices. Specifically, for example, when no significant increase in circulating leptin levels were observed even under the conditions where leptin resistance would be induced (e.g. as will be mentioned later, high-fat diet is given for a long time), it can be evaluated that leptin resistance is prevented. Further, when a state where leptin resistance was induced (e.g. as will be mentioned later, a state where high-fat diet induced leptin resistance. In this state, circulating leptin levels would increase) was changed to a state where circulating leptin levels were significantly decreased, it can be evaluated that leptin resistance is ameliorated.

The pharmaceutical composition of the present invention may further contain a component other than flurbiprofen (e.g. pharmaceutically acceptable carrier) which does not prevent the effect yielded by flurbiprofen.

The "pharmaceutically acceptable carrier" is explained below. In the specification, the "pharmaceutically acceptable carrier" (which may be hereinafter referred to as merely "carrier") is a substance which is used in production of medical drugs or agricultural chemicals such as veterinary medicine for the purpose of assisting prescription and which does not have an adverse effect on an effective component. Further, the carrier is intended to be a substance which does not have toxic consequences and does not induce production of a harmful antibody in an individual having received the pharmaceutical composition of the present invention.

Examples of the carrier include various organic or nonorganic carrier substances usable as drug raw materials, and may be suitably selected according to a later-mentioned administration form and dosage form of the pharmaceutical composition. For example, the carrier is mixed as a diluting agent, a lubricant, a binding agent, a disintegrant etc. in solid medicine; a solvent, a solubilizing agent, a suspending agent, a tonicity agent, a buffer, a soothing agent etc. in liquid medicine; an antiseptic agent; an antioxidant; a stabilizer; a flavoring substance etc. However, the present invention is not limited to these.

Examples of the "diluting agent" include lactose, saccharose, D-mannitol, xylitol, sorbitol, erythritol, starch, crystalline cellulose etc. However, the "diluting agent" is not particularly limited as long as it is normally used in the field of medicine manufacture.

Examples of the "lubricant" include magnesium stearate, calcium stearate, wax, talc, and colloid silica. However, the "lubricant" is not particularly limited as long as it is normally used in the field of medicine manufacture.

Examples of the "binding agent" include pregelatinized starch, methylcellulose, crystalline cellulose, saccharose, D-mannitol, trehalose, dextrin, hydroxypropylcellulose, hydroxypropylmethylcellulose, and polyvinylpyrrolidone. However, the "binding agent" is not particularly limited as long as it is normally used in the field of medicine manufacture.

Examples of the "disintegrant" include starch, carboxymethylcellulose, low substituted hydroxypropylcellulose, carboxymethylcellulose calcium, croscarmellose sodium, and carboxymethyl starch sodium. However, the disintegrant" is not particularly limited as long as it is normally used in the field of medicine manufacture.

Examples of the "solvent" include an injection solvent, alcohol, propylene glycol, macrogol, sesame oil, cone oil, and tricaprylin. However, the "solvent" is not particularly limited as long as it is normally used in the field of medicine manufacture.

Examples of the "solubilizing agent" include polyethyleneglycol, propyleneglycol, D-mannitol, trehalose, benzyl benzoate, ethanol, trisaminomethane, cholesterol, triethanol amine, sodium carbonate, and sodium citrate. However, the "solubilizing agent" is not particularly limited as long as it is normally used in the field of medicine manufacture.

Examples of the "suspending agent" include: surfactants such as stearyl triethanol amine, sodium lauryl sulfate, lauryl amino propionic acid, lecithin, benzalkonium chloride, benzethonium chloride and glycerin monostearate; and hydrophilic macromolecules such as polyvinyl alcohol, polyvinyl pyrrolidone, sodium carboxymethylcellulose, methylcellulose, hydroxymethylcellulose, hydroxyethylcellulose, and hydroxypropylcellulose. However, the suspending agent" is not particularly limited as long as it is normally used in the field of medicine manufacture.

Examples of the "tonicity agent" include sodium chloride, glycerin, and D-mannitol. However, the "tonicity agent" is not particularly limited as long as it is normally used in the field of medicine manufacture.

Examples of the "buffer" include buffer solutions such as phosphate, acetate, carbonate, and citrate. However, the "buffer" is not particularly limited as long as it is normally used in the field of medicine manufacture.

Examples of the "soothing agent" include benzyl alcohol. However, the "soothing agent" is not particularly limited as long as it is normally used in the field of medicine manufacture.

Examples of the "antiseptic agent" include paraoxy benzoic esters, chlorobutanol, benzyl alcohol, phenethyl alcohol, dehydroacetic acid, and sorbic acid. However, the "antiseptic agent" is not particularly limited as long as it is normally used in the field of medicine manufacture.

Examples of the "antioxidant" include sulfite salt and ascorbic acid. However, the "antioxidant" is not particularly limited as long as it is normally used in the field of medicine manufacture.

Further, the stabilizer and the flavoring substance are not particularly limited as long as they are normally used in the field of medicine manufacture.

Administration form for the pharmaceutical composition of the present invention may be oral administration or non-oral administration such as intravenous administration, intrarectal administration, intraperitoneal administration, intramuscular administration, and subcutaneous administration. An appropriate administration path may be selected according to the form of medicine. Among them, it is preferable that the composition of the present invention is administered orally since oral administration is easy.

In the specification, the term "non-oral administration" means administration by intraventricular injection or infusion, intravenous injection or infusion, intramuscular injection or infusion, intraperitoneal injection or infusion, intrasternal injection or infusion, subcutaneous injection or infusion, or intraarticular injection or infusion.

In a case where the pharmaceutical composition of the present invention is administered orally, examples of the dosage form of such a pharmaceutical composition (which may be hereinafter referred to as "orally administered drug") include solid medicine such as dusting powder, granule, a tablet, liposome, a capsule (including soft capsule and microcapsule), and powder medicine, and liquid medicine such as syrup.

The "liquid medicine" may be produced by a method normally employed in the field of medicine manufacture with use of water, organic solvents such as glycerol, glycol, and polyethyleneglycol, mixtures of these organic solvents and water etc. as the carrier. The liquid medicine may further contain a solubilizing agent, a buffer, a tonicity agent, a stabilizer etc.

The "solid medicine" may be produced by a method normally employed in the field of medicine manufacture with use of a diluting agent, a lubricant, a binding agent, a disintegrant, a stabilizer, a flavoring substance etc. as the carrier.

When preparing such an orally administered drug, a lubricant, a liquidity promoting agent, a coloring agent, fragrant material etc. may be further mixed according to the purpose.

In a case where the pharmaceutical composition of the present invention is administered non-orally, the dosage form of such a pharmaceutical composition (which may be hereinafter referred to as "non-orally administered drug") may be an injectable solution, a suppository, a pellet, drops etc. Such a non-orally administered drug can be prepared by solving or suspending the pharmaceutical composition of the present invention in a thinner (e.g. distilled water for injection, physiological saline, glucose aqueous solution, vegetable oil for injection, sesame oil, peanut oil, soybean oil, cone oil, propyleneglycol, polyethyleneglycol) according to a method publicly known in the field of medicine manufacture and further adding a disinfectant, a stabilizer, a tonicity agent, a soothing agent etc. to the mixture according to the purpose.

Further, the pharmaceutical composition of the present invention may be prepared as sustained release preparation by a technique normally employed in the field of medicine manufacture.

The pharmaceutical composition of the present invention may be administered solely or in combination with other drug. In a case where the pharmaceutical composition is administered in combination with other drug, the pharmaceutical composition may be administered simultaneously with other drug in the form of a mixture with other drug, or may be administered independently from other drug but simultaneously or in parallel with other drug, or administered with time. However, the present invention is not limited to this.

The number of administration of the pharmaceutical composition of the present invention per day is not particularly limited. The number of administration may be one per day or plural per day as long as the administration amount of flurbiprofen is within the range of the required administration amount per day.

A person skilled in the art can easily understand that the pharmaceutical composition of the present invention is also applicable to mammals other than humans (e.g. mice, rats, rabbits, dogs, cats, cattle, horses, pigs, and monkeys).

The present invention is described above using preferable embodiments. However, the present invention is not limited to the descriptions of the embodiments above, but may be altered by a skilled person within the scope of the claims. An embodiment based on a proper combination of technical means appropriately modified within the scope of the claims is encompassed in the technical scope of the present invention.

EXAMPLES

The following further specifically explains the present invention using Examples. It should be noted that the present invention is not limited to these Examples.

In the Examples, 4 weeks-old male mice (C57BL/6 Cr Slc, SHIMIZU Laboratory Supplies Co., Ltd.) were used as laboratory animals. All the animal tests in the Examples were carried out according to the NIH Guide for Care and Use of Laboratory Animals.

Example 1

Effect 1 of Flurbiprofen on Leptin Resistance (How to Induce Leptin Resistance and how to Confirm Leptin Resistance)

Initially, the following explains how leptin resistance was induced and how leptin resistance was confirmed in the present Example.

FIG. 1 is a graph showing changes in body weights of mice which had been given high-fat diet or normal diet. Values in the graph of FIG. 1 are averages of body weights of mice of each group (± their standard deviations) (n=7-8 with respect to each group). Further, statistic analysis was carried out using t-test. "" in FIG. 1 indicates that there is a significant difference, with significance level of less than 1%, in body weight between the group which had been given high-fat diet and the group which had been given normal diet. Further, "*" indicates that there is a significant difference, with significance level of less than 0.1%, in body weight between the group which had been given high-fat diet and the group which had been given normal diet.

As shown in FIG. 1, the mice which had been given high-fat diet (60 kcal % fat, D12492, produced by Research Diets, Inc.) exhibited a significant increase in body weight compared with the mice which had been given normal diet (10 kcal % fat, D12450B, produced by Research Diets, Inc.).

Subsequently, a solution prepared by solving mouse-derived leptin (450-31, produced by PeproTech Inc. or 498-OB, rmLeptin, produced by R&D systems) in physiological saline was non-orally administered via tail vein to the mice which had been given high-fat diet or normal diet for 16 weeks. The non-oral administration was done in such a manner that the administration amount of leptin would be 5 ml/kg (1 mg/kg). As a control for leptin administration, physiological saline in equal amount was administered to the mice via tail vein.

Figure 2:
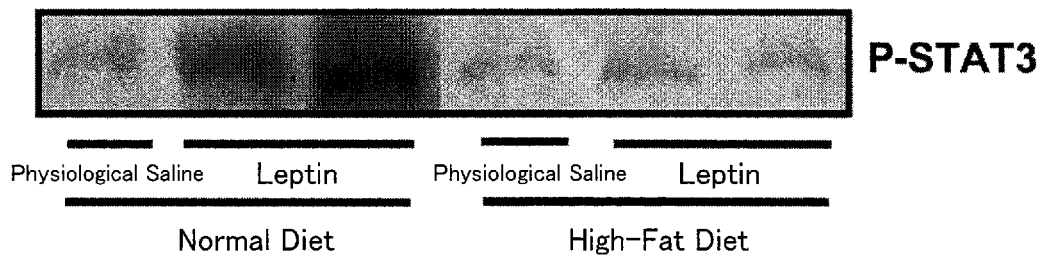
FIG. 2 is a drawing showing that giving high-fat diet induces leptin resistance.

FIG. 2 shows the result of Western blotting of the STAT3 phosphorylation in hypothalami of mice 30 minutes after leptin injection. For the Western blotting, an antibody which recognizes phosphorylated STAT3 (9131S, produced by Cell Signaling Technology, Inc.) was used. As shown in FIG. 2, in the mice which had been given high-fat diet for 16 weeks, STAT3 phosphorylation in hypothalami was prevented even after the leptin administration. This indicates that a leptin's signal was prevented in hypothalami even after the leptin administration. The result indicates that leptin resistance was induced.

From the results of FIGS. 1 and 2, it was confirmed that giving high-fat diet for a long time can induce leptin resistance. Further, it was confirmed that an increase in body weight of mice is related to prevention of STAT3 phosphorylation in hypothalamus. This indicates that whether leptin resistance is present or not can also be evaluated by measuring the increase in the body weight of mice. Accordingly, in the present Example, leptin resistance was induced by giving high-fat diet for a long time, and then the changes in body weights of mice were observed as a reference index to confirm whether or not the leptin resistance was ameliorated and/or prevented by the administration of flurbiprofen.
[Test]

Mice were divided into four groups each consisting of 7-8 mice. Mice of individual groups were given diets as follows.
Group 1: Normal diet (10 kcal % fat, D12450B, produced by Research Diets, Inc.) only
Group 2: High-fat diet (60 kcal % fat, D12492, produced by Research Diets, Inc.) only
Group 3: Normal diet+flurbiprofen (F8514, produced by SIGMA)
Group 4: High-fat diet+flurbiprofen (F8514, produced by SIGMA)

Flurbiprofen was diluted with drinking water so that the administration amount of flurbiprofen would be approximately 10 mg/kg per day, and was orally administered to the mice in the form of drinking water. Thereafter, the mice were weighed every 7 days.
(Result)

Figure 3:
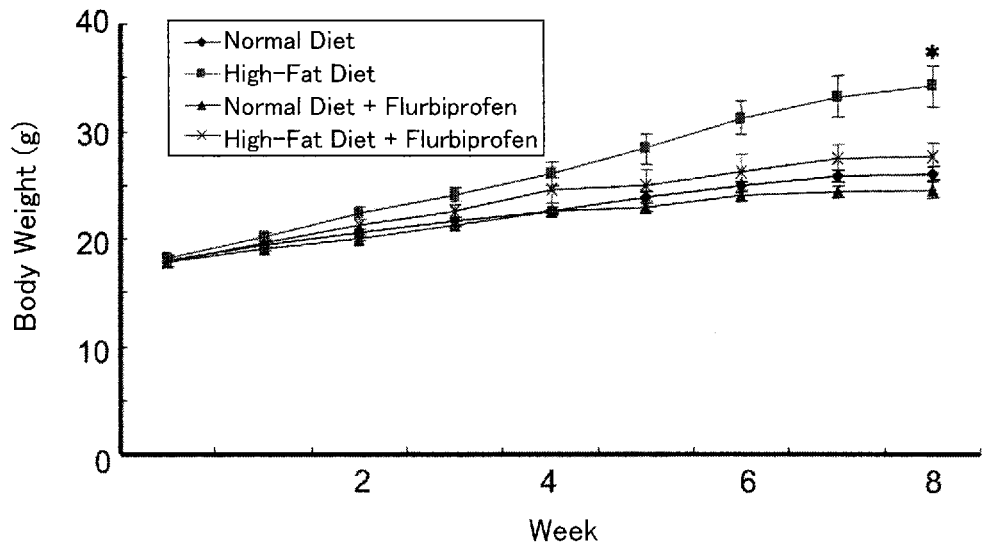
FIG. 3 is a graph showing changes in body weights of mice of individual groups to which flurbiprofen had been administered for 8 weeks.

FIG. 3 shows the result of the test. FIG. 3 is a graph showing changes in body weights of the mice of individual groups during 8 weeks after flurbiprofen administration. Values in the graph of FIG. 3 are averages of body weights of mice of each group (± their standard deviations) (n=7-8 with respect to each group). Further, statistic analysis was carried out using t-test. "*" in the graph indicates that there is a significant difference in body weight between Group 2 and Group 4 with significance level of less than 5%.

As shown in FIG. 3, at 8 weeks after flurbiprofen administration, a significant difference in body weight between Group 2 and Group 4 was observed. This indicates that administration of flurbiprofen prevented an increase in body weight of Group 4. In the above section which indicates "How to induce leptin resistance and how to confirm leptin resistance", the result of FIG. 2 shows that giving high-fat diet to mice can induce leptin resistance in the mice. Further, in that section, it was shown that whether leptin resistance is present or not can also be evaluated by measuring the increase in body weight of mice. As shown in FIG. 3, Group 2, which had been given high-fat diet, exhibited an increase in body weight compared with Group 1, which had been given normal diet. It obviously indicates that leptin resistance was induced in Group 2. On the other hand, although Group 4 had been given high-fat diet similarly with Group 2, Group 4 did not exhibit an increase in body weight compared with Group 1, which had been given normal diet. From this result, it is inferred that giving high-fat diet to Group 4 would have induced leptin resistance under normal circumstances, but administration of flurbiprofen to Group 4 prevented induction of leptin resistance.

On the other hand, there was no significant difference in body weight between Groups 1 and 3 which had been given normal diet. From this result, it can be confirmed that the decrease in body weight was not caused by induction of toxicity or side-effect derived from administration of flurbiprofen.

Example 2

Effect 2 of Flurbiprofen on Leptin Resistance (How to Induce Leptin Resistance and how to Confirm Leptin Resistance)

4 weeks-old male mice (C57BL/6 Cr Slc) had been given normal diet (10 kcal % fat, D12450B, produced by Research Diets, Inc.) or high-fat diet (60 kcal % fat, D12492, produced by Research Diets, Inc.). Flurbiprofen was diluted with drinking water so that the administration amount of flurbiprofen would be approximately 10 mg/kg per day, and was orally administered to the mice in the form of drinking water.

Specifically, mice were divided into four groups each consisting of 7-8 mice. Mice of individual groups were given diets as follows.
Group 1: Normal diet (10 kcal % fat) only
Group 2: High-fat diet (60 kcal % fat) only
Group 3: Normal diet+flurbiprofen
Group 4: High-fat diet+flurbiprofen A solution prepared by solving mouse-derived leptin (450-31, produced by PeproTech Inc. or 498-OB, rmLeptin, produced by R&D systems) in physiological saline was non-orally administered via tail vein to the mice, which had been given high-fat diet or normal diet for 8 weeks. The non-oral administration was done in such a manner that the administration amount of leptin would be 1 mg/kg. As a control for leptin administration, physiological saline in equal amount was administered to the mice via tail vein.

Figure 4:
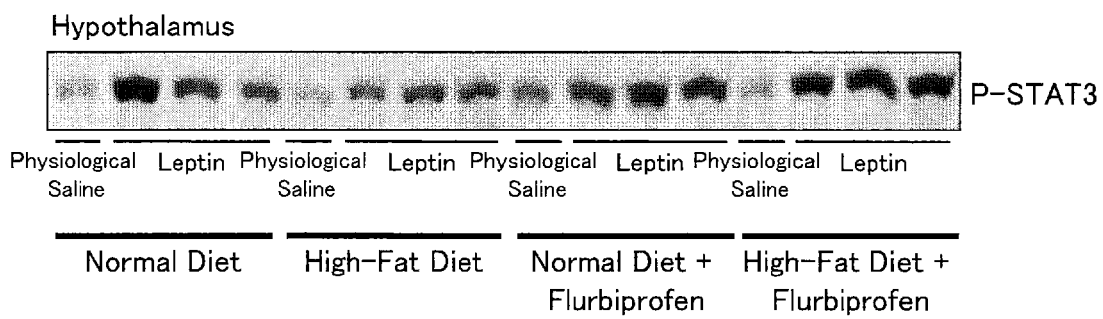
FIG. 4 is a drawing showing the result of Western blotting of STAT3 phosphorylation in hypothalami of mice of individual groups 30 min after leptin injection.
Figure 5:
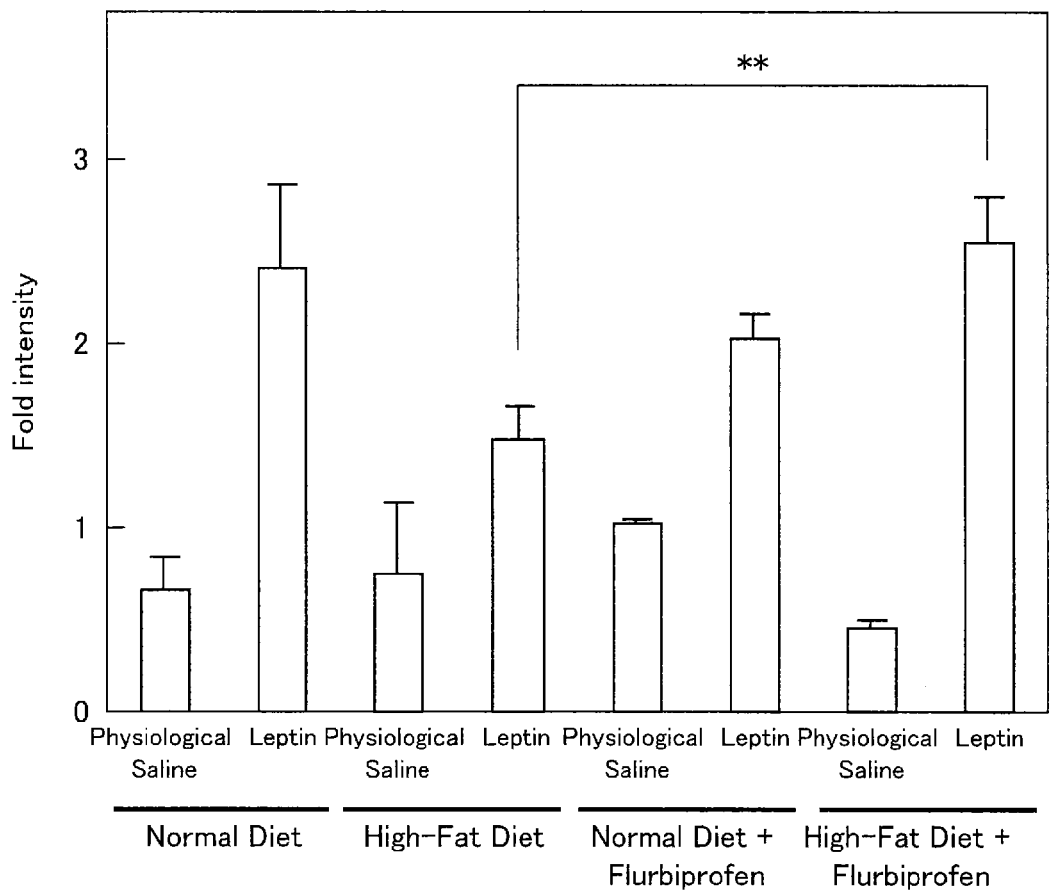
FIG. 5 is a graph obtained by expressing the result of the Western blotting in FIG. 4 in numerical values. Longitudinal axis in FIG. 5 indicates intensity of STAT3 phosphorylation in hypothalami of the mice of individual groups.

FIGS. 4 and 5 show the result of Western blotting of STAT3 phosphorylation in hypothalami of mice 30 minutes after leptin injection. For the Western blotting, an antibody which recognizes phosphorylated STAT3 (9131S, produced by Cell Signaling Technology, Inc.) was used. FIG. 4 shows the result of Western blotting of STAT3 phosphorylation in hypothalami of mice 30 minutes after leptin injection. FIG. 5 is a graph obtained by expressing the result of the Western blotting in FIG. 4 in numerical values. The longitudinal axis in FIG. 5 indicates intensity of STAT3 phosphorylation in hypothalami of the mice of individual groups. Values in the graph of FIG. 5 are averages of intensities of STAT3 phosphorylation in hypothalami of mice of each group (± their standard deviations) (n=7-8 with respect to each group). Further, statistic analysis was carried out using t-test. "**" in FIG. 5 indicates that there is a significant difference, with significance level of less than 1%, in intensity of STAT3 phosphorylation in hypothalami between mice of Group 2 which had been given high-fat diet for 8 weeks before leptin administration and mice of Group 4 which had been given high-fat diet with flurbiprofen for 8 weeks before leptin administration.

As shown in FIG. 4, in the mice which had been given high-fat diet for 8 weeks, STAT3 phosphorylation in hypothalami was prevented even after leptin administration. This indicates that a leptin's signal was prevented in the hypothalami even after leptin administration. The result indicates that leptin resistance was induced. In contrast thereto, in the mice which had been given high-fat diet with flurbiprofen for 8 weeks, STAT3 in hypothalami was phosphorylated after leptin administration. Further, as shown in FIG. 5, intensity of STAT3 phosphorylation in hypothalami of mice of Group 4, which had been given high-fat diet with flurbiprofen, was significantly higher than that of mice of Group 2, which had been given high-fat diet. From these results, it is found that simultaneous administration of high-fat diet with flurbiprofen can inhibit prevention of STAT3 phosphorylation caused due to long-time intake of high-fat diet. That is, simultaneous administration of high-fat diet with flurbiprofen can prevent induction of leptin resistance.

Example 3

Effect of Flurbiprofen on Increased Circulating Leptin Levels (How to Increase Circulating Leptin Levels and how to Confirm Circulating Leptin Levels)

4 weeks-old male mice (C57BL/6 Cr Slc) had been given normal diet (10 kcal % fat, D12450B, produced by Research Diets, Inc.) or high-fat diet (60 kcal % fat, D12492, produced by Research Diets, Inc.). Flurbiprofen was diluted with drinking water so that the administration amount of flurbiprofen would be approximately 10 mg/kg per day, and was orally administered to the mice in the form of drinking water.

Specifically, mice were divided into four groups each consisting of 7-8 mice. Mice of individual groups were given diets as follows.
Group 1: Normal diet (10 kcal % fat) only
Group 2: High-fat diet (60 kcal % fat) only
Group 3: Normal diet+flurbiprofen
Group 4: High-fat diet+flurbiprofen 20-25 µL of blood samples before or after fasting for 28-29.5 hours were obtained from mice via tail vein, which had been given high-fat diet or normal diet for 8 weeks. The blood samples were mixed with 1 µL of 0.5 M EDTA and the mixtures were subjected to centrifugation (3000 rpm, 15 minutes). Plasma leptin levels in the supernatants obtained by the centrifugation were measured by ELISA.

Figure 6:
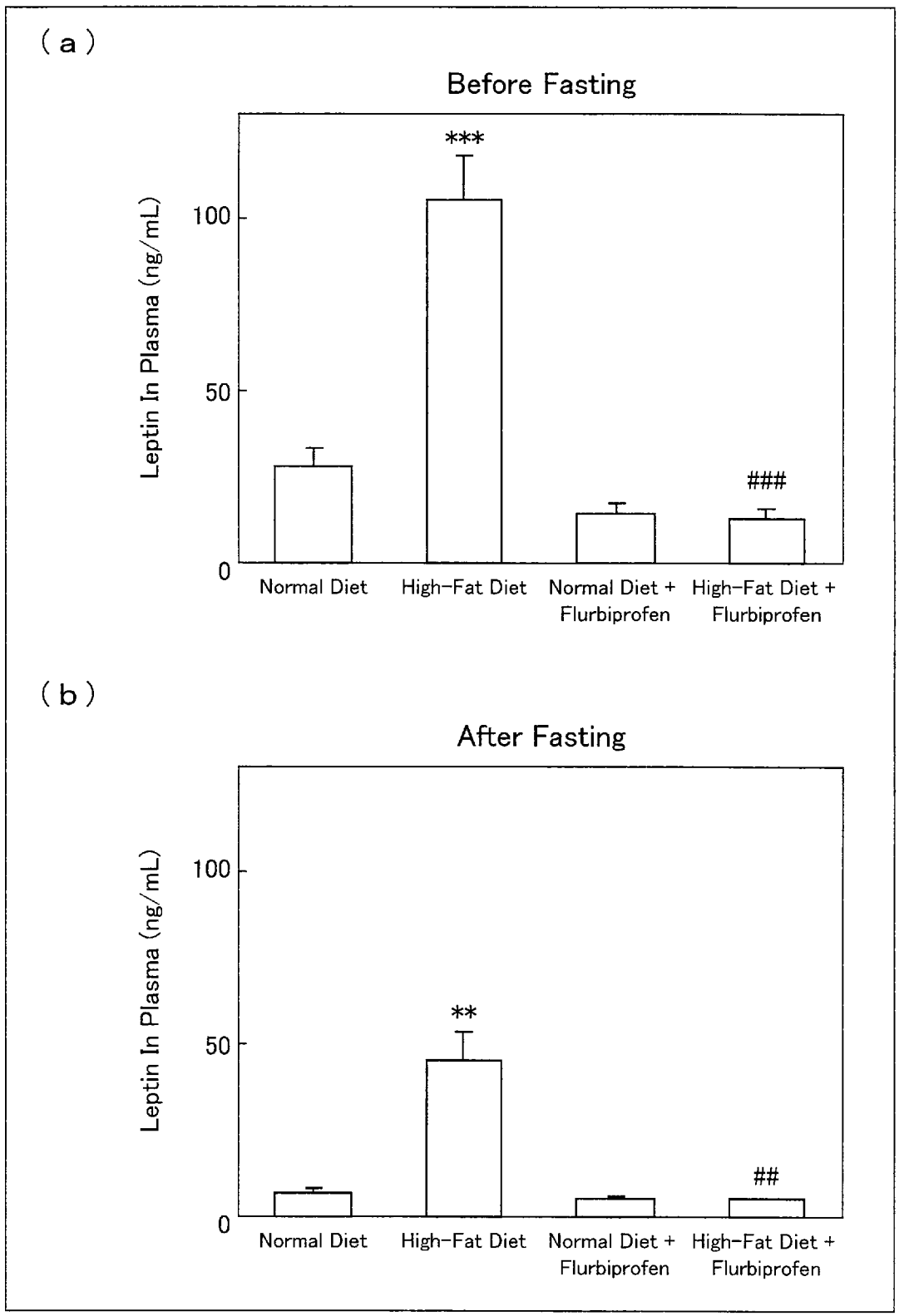
FIG. 6 is a graph showing the result of measuring plasma leptin levels before and after fasting. (a) of FIG. 6 shows plasma leptin levels measured before fasting. (b) of FIG. 6 shows plasma leptin levels measured after fasting.
Figure 7:
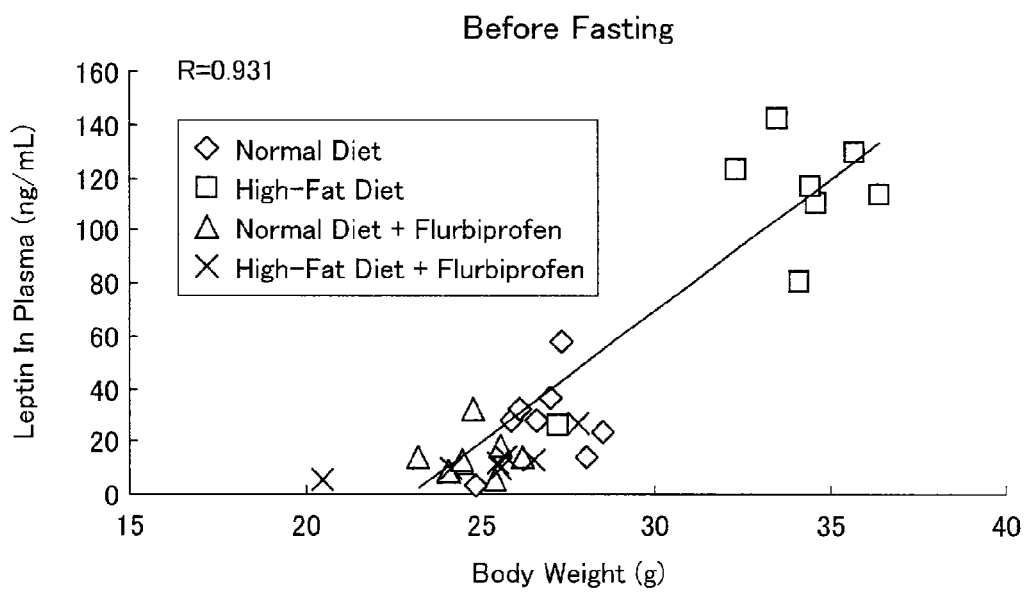
FIG. 7 is a graph showing a correlation between plasma leptin levels and body weight. (a) of FIG. 7 shows a correlation between plasma leptin levels and body weight measured before fasting. (b) of FIG. 7 shows a correlation between plasma leptin levels and body weight measured after fasting.
Figure 7:
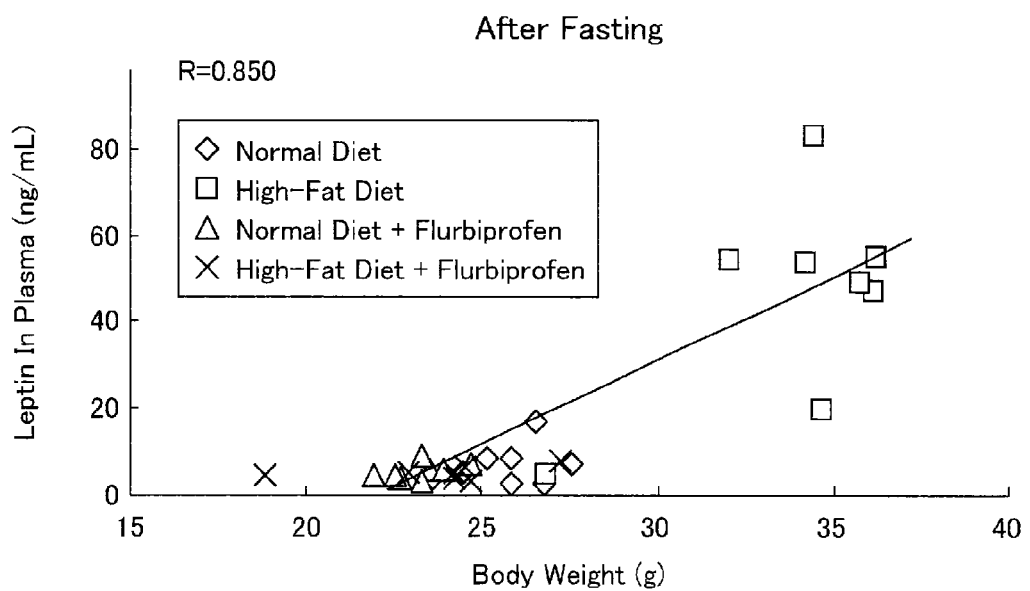

FIGS. 6 and 7 show the result. FIG. 6 is a graph showing the result of measuring plasma leptin levels before and after fasting. (a) of FIG. 6 shows plasma leptin levels measured before fasting. (b) of FIG. 6 shows plasma leptin levels measured after fasting. Values in the graph of (a) of FIG. 6 are averages of plasma leptin levels of mice of each group measured before fasting (± their standard deviations) (n=7-8 with respect to each group). Similarly, values in the graph of (b) of FIG. 6 are averages of plasma leptin levels of mice of each group measured after fasting (± their standard deviations) (n=7-8 with respect to each group). Further, statistic analysis was carried out using t-test. "*" in FIG. 6 indicates that there is a significant difference, with significance level of less than 0.1%, in plasma leptin levels measured before fasting between mice of Group 2 which had been given high-fat diet for 8 weeks and mice of Group 1 which had been given normal diet. "" indicates that there is a significant difference, with significance level of less than 1%, in plasma leptin levels measured after fasting between mice of Group 2 which had been given high-fat diet for 8 weeks and mice of Group 1 which had been given normal diet. Further, "###" in FIG. 6 indicates that there is a significant difference, with significance level of less than 0.1%, in plasma leptin levels measured before fasting between mice of Group 4 which had been given high-fat diet with flurbiprofen for 8 weeks and mice of Group 2 which had been given high-fat diet. "##" indicates that there is a significant difference, with significance level of less than 1%, in plasma leptin levels measured after fasting between mice of Group 4 which had been given high-fat diet with flurbiprofen for 8 weeks and mice of Group 2 which had been given high-fat diet.

FIG. 7 is a graph showing a correlation between plasma leptin levels and body weight. (a) of FIG. 7 shows a correlation between plasma leptin levels and body weight measured before fasting. (b) of FIG. 7 shows a correlation between plasma leptin levels and body weight measured after fasting. "R" in FIG. 7 indicates a correlation coefficient.

As shown in FIG. 6, the mice of Group 2, which had been given high-fat diet for 8 weeks, exhibited significantly higher plasma leptin levels before and after fasting, compared with the mice of Group 1, which had been given normal diet. On the other hand, the mice of Group 4, which had been given high-fat diet with flurbiprofen for 8 weeks, exhibited significantly lower plasma leptin levels compared with the mice of Group 2, which had been given high-fat diet. Further, as shown in FIG. 7, there was a correlation between body weight of the mice and plasma leptin levels measured before and after fasting. From these results, it is found that simultaneous administration of high-fat diet with flurbiprofen can prevent an increase in plasma leptin levels.

In an individual in which leptin resistance is induced, leptin fails to function. To overcome this failure, the homeostatic regulatory system is operated. Activation of this system causes increased secretion of leptin in the blood stream. Consequently, the individual in which leptin resistance is induced has higher leptin levels in the blood stream. In contrast thereto, in a mouse of Group 4 which had been given high-fat diet with flurbiprofen for 8 weeks, leptin resistance is prevented. As leptin functions normally, it is unnecessary to secrete more amount of leptin. Therefore, it is considered that in a mouse of Group 4 which had been given high-fat diet with flurbiprofen for 8 weeks, leptin levels in the blood stream are kept in a normal value.

Example 4

Effect of Decreasing Blood Glucose Level by Flurbiprofen

It has been reported that leptin resistance contributes to the onset of diabetes (see, for example, Gwo-Hwa Lee et al, Abnormal splicing of the leptin receptor in diabetic mice, Nature 1996, 379(15):632-635; Hong Chen et al, Evidence That the Diabetes Gene Encodes the Leptin Receptor: Identification of a Mutation in the Leptin Receptor Gene in db/db Mice, Cell 1996, 84: 491-495 etc.). Specifically, db/db mice having mutations in a high-affinity receptor for leptin (OB-R) and deficiency in transmission of a leptin's signal develop diabetes. Accordingly, measuring a change in blood glucose level by a glucose tolerance test as a reference index will be useful to examine whether leptin resistance is induced or not.

In view of the above, Example 4 discussed whether it is possible to evaluate induction of leptin resistance by measuring a change in blood glucose level by the glucose tolerance test as a reference index. At the same time, Example 4 discussed whether administration of flurbiprofen can prevent induction of leptin resistance, by measuring a change in blood glucose level by the glucose tolerance test as a reference index. Specifically, 4 weeks-old mice (C57BL/6 Cr Slc) were divided into four groups each consisting of 14-16 mice. Mice of individual groups were given diets as follows for 8 weeks similarly with Example 3.
Group 1: Normal diet (10 kcal % fat) only
Group 2: High-fat diet (60 kcal % fat) only
Group 3: Normal diet+flurbiprofen
Group 4: High-fat diet+flurbiprofen Flurbiprofen (F8514, produced by SIGMA) was diluted with drinking water so that the administration amount of flurbiprofen would be 10 mg/kg per day, and was orally administered to the mice in the form of drinking water.

The mice of individual groups were subjected to the glucose tolerance test after intake of high-fat diet or normal diet for 8 weeks.
(Glucose Tolerance Test)

The glucose tolerance test is the most basic method for evaluating glucose tolerance and insulin secretory function. In Example 4, mice were fasted overnight for 17 hours, and fasted blood glucose level (pre) was measured by Freestyle freedom (NIPRO CORPORATION, blood glucose self-monitoring system) at 10:00 a.m. Thereafter, glucose was intraperitoneally (i.p.) administered so that the administration amount of glucose would be 2 g/kg. Blood glucose level was measured by Freestyle freedom (NIPRO CORPORATION, blood glucose self-monitoring system) 30 minutes, 1 hour, and 2 hours after the administration.

Figure 8:
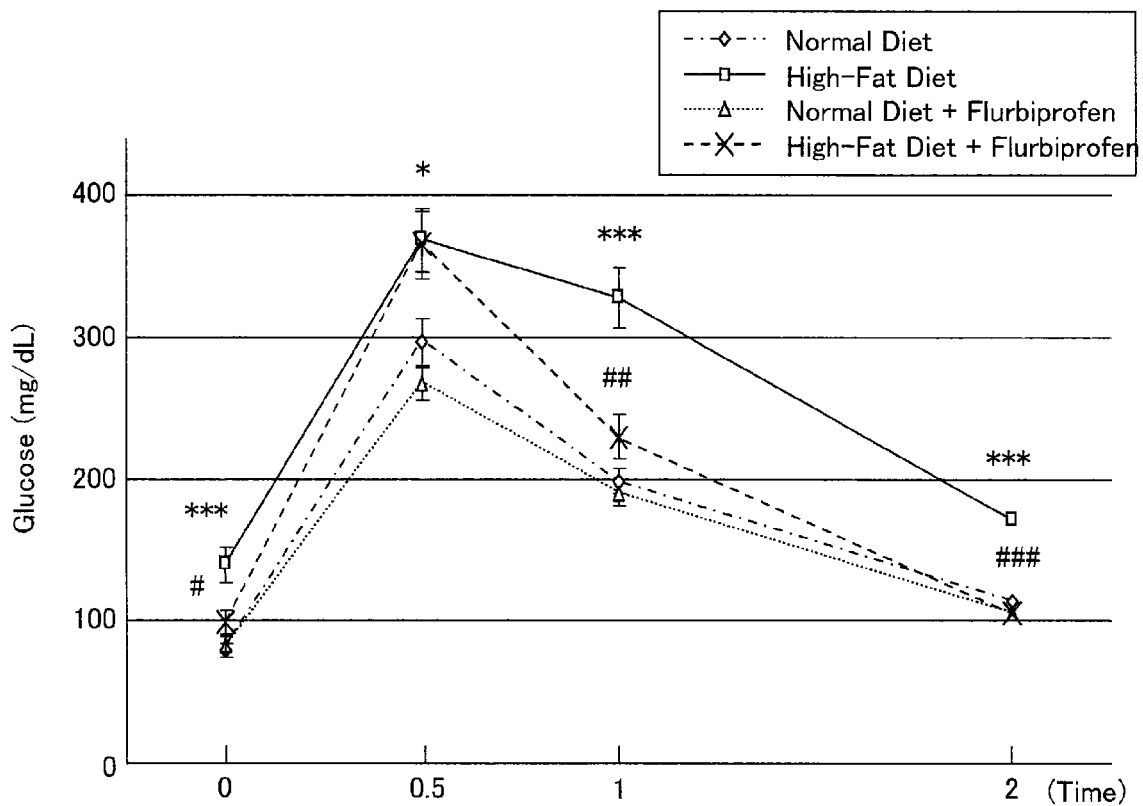
FIG. 8 is a graph showing the result of a glucose tolerance test.

FIG. 8 shows the result. FIG. 8 is a graph showing the result of the glucose tolerance test. Values in the graph of FIG. 8 are averages of blood glucose levels of the mice of each group (± their standard deviations) (n=14-16 with respect to each group). Further, statistic analysis was carried out using t-test. "*" in FIG. 8 indicates that there is a significant difference, with significance level of less than 5%, in blood glucose level between the mice of Group 2 which had been given high-fat diet for 8 weeks and the mice of Group 1 which had been given normal diet. "***" indicates that there is a significant difference with significance level of less than 0.1%.

Further, "#" in FIG. 8 indicates that there is a significant difference, with significance level of less than 5%, in blood glucose level between the mice of Group 4 which had been given high-fat diet with flurbiprofen for 8 weeks and the mice of Group 2 which had been given high-fat diet. "##" indicates that there is a significant difference with significance level of less than 1%. "###" indicates that there is a significant difference with significance level of less than 0.1%.

As shown in FIG. 8, the mice of Group 2 which had been given high-fat diet exhibited a significantly higher blood glucose level 2 hours after glucose administration, compared with the mice of Group 1 which had been given normal diet. As described in Examples 1 to 3, it was found that giving high-fat diet for 8 weeks induces leptin resistance. Accordingly, the result of FIG. 8 shows that whether leptin resistance is present or not can also be evaluated by examining a change in blood glucose level by the glucose tolerance test.

Further, the mice of Group 4 exhibited a rapidly decreased blood glucose level 1 hour after glucose administration, similarly with the mice of Groups 1 and 3 which were controls without leptin resistance. Further, a significant difference in blood glucose levels between Group 2 and Group 4 was observed 1 hour after glucose administration. In view of the above, using the change in blood glucose level in the glucose tolerance test as a reference index, it was confirmed that administration of flurbiprofen can prevent induction of leptin resistance.

In contrast thereto, there was no significant difference in blood glucose level between Group 1 and Group 3 which had been given normal diet. In view of the above, it was confirmed that flurbiprofen does not directly decrease blood glucose level.

Example 5

Effect of Flurbiprofen on High-Fat Diet-Induced Accumulation of Fat Content in Mice 4 weeks-old mice (C57BL/6 Cr Slc) were divided into four groups each consisting of 7-8 mice. Mice of individual groups were given diets as follows for 8 weeks similarly with Example 4.
Group 1: Normal diet (10 kcal % fat) only
Group 2: High-fat diet (60 kcal % fat) only
Group 3: Normal diet+flurbiprofen
Group 4: High-fat diet+flurbiprofen Flurbiprofen (F8514, produced by SIGMA) was diluted with drinking water so that the administration amount of flurbiprofen would be 10 mg/kg per day, and was orally administered to the mice in the form of drinking water.

The mice raised for 8 weeks with high-fat diet or normal diet were cut open along a median line, and the amount of fatty tissue (visceral fat) was measured. Visceral fat was extracted from the abdomen of a mouse, and wet weight of the fat was measured.

Figure 9:
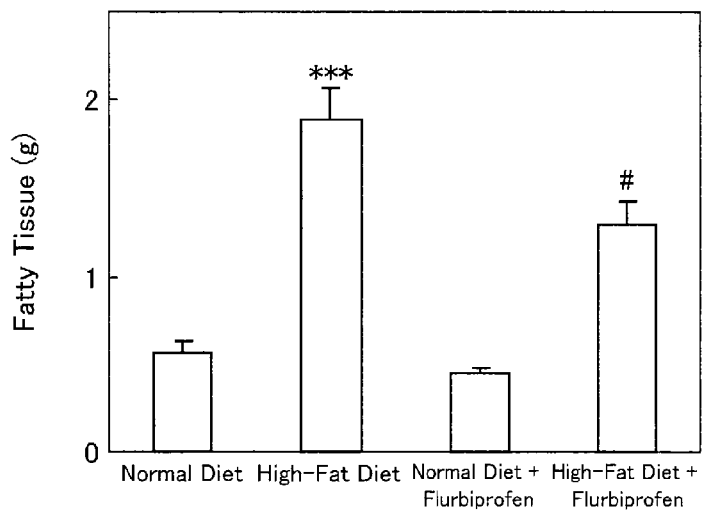
FIG. 9 is a graph showing the amount of fat content of mice of individual groups, to which flurbiprofen had been administered for 8 weeks.

FIG. 9 shows the result. FIG. 9 is a graph showing the amounts of fat contents of mice of individual groups to which flurbiprofen had been administered for 8 weeks. Values in the graph of FIG. 9 are averages of the amounts (g) of fat of mice of each group (± their standard deviations) (n=7-8 with respect to each group). Further, statistic analysis was carried out using t-test. "***" in FIG. 9 indicates that there is a significant difference, with significance level of less than 0.1%, in the amount of fat content between the mice of Group 2 which had been given high-fat diet for 8 weeks and the mice of Group 1 which had been given normal diet. "#" indicates that there is a significant difference, with significance level of less than 5%, in the amount of fat content between the mice of Group 4 which had been given high-fat diet with flurbiprofen for 8 weeks and the mice of Group 2 which had been given high-fat diet.

As shown in FIG. 9, the mice of Group 2 which had been given high-fat diet for 8 weeks exhibited a significant increase in the amount of fat content, compared with the mice of Group 1 which had been given normal diet. Further, the mice of Group 4 which had been given high-fat diet with flurbiprofen for 8 weeks exhibited a significant decrease in the amount of fat content, compared with the mice of Group 2 which had been given high-fat diet for 8 weeks.

Example 6

Influence of High-Fat Diet with Flurbiprofen on Amounts of Mice Activity

In order to measure the amounts of mice activity, an Open Field Test was carried out. Specifically, 4 weeks-old male mice (C57BL/6 Cr Slc) were divided into four groups each consisting of 15-16 mice. Mice of individual groups were given diets as follows for 8 weeks similarly with Example 5.
Group 1: Normal diet (10 kcal % fat) only
Group 2: High-fat diet (60 kcal % fat) only
Group 3: Normal diet+flurbiprofen
Group 4: High-fat diet+flurbiprofen Flurbiprofen (F8514, produced by SIGMA) was diluted with drinking water so that the administration amount of flurbiprofen would be 10 mg/kg per day, and was orally administered to the mice in the form of drinking water.

The mice raised for 8 weeks with high-fat diet or normal diet were subjected to the Open Field Test.

(Open Field Test)

The Open Field Test is a test in which mice were put at the center of a square field (48×48 cm) and the amounts of activity of the mice in the new environment were measured in numerals. Specifically, with respect to each of the mice, the amount of activity per 5 minutes was measured using a locomotor activity measuring device (SCANET MV-10MT, produced by Toyo Sangyo Co., Ltd.). The measurements were performed between 16:30 and 17:30 which was a time before feeding behavior of the mice would become active.

Figure 10:
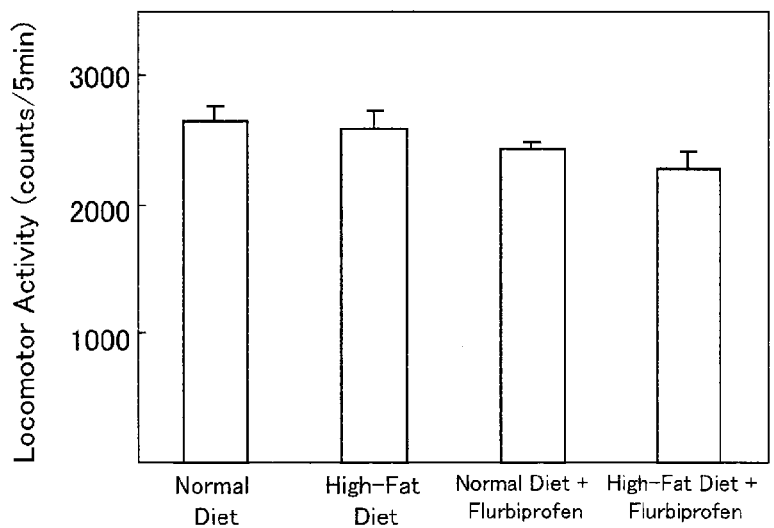
FIG. 10 is a graph showing the amounts of activity of mice of individual groups, to which flurbiprofen had been administered for 8 weeks.

FIG. 10 shows the result. FIG. 10 is a graph showing the amounts of activity of mice of individual groups to which flurbiprofen had been administered for 8 weeks. Values in the graph of FIG. 10 are averages of the amounts of activities (locomotor activity (counts/5 min) of mice of each group (± their standard deviations) (n=15-16 with respect to each group). Further, statistic analysis was carried out using t-test.

As shown in FIG. 10, there was no significant difference in the amounts of activity between the mice of Group 2 which had been given high-fat diet and the mice of Group 1 which had been given normal diet. Further, there was no significant difference in the amounts of activity between the mice of Group 1 or 2 to which flurbiprofen had not been administered and the mice of Group 3 or 4 to which flurbiprofen had been administered.

From these results, it was confirmed that high-fat diet or administration of flurbiprofen does not have an influence on the amounts of mice activity.

Example 7

Prevention of Leptin Resistance by Flurbiprofen—Analysis on Food Intake

When leptin resistance is induced, the effects of leptin on inhibiting food intake and enhancing energy expenditure are attenuated in spite of increased leptin levels in the blood stream. Accordingly, whether leptin resistance is present or not can be confirmed by measuring the action of leptin-induced inhibition of food intake as a reference index. In Example 7, using this reference index, it was further confirmed that flurbiprofen can prevent induction of leptin resistance.

Specifically, 4 weeks-old male mice (C57BL/6 Cr Slc) were divided into four groups each consisting of 6-8 mice. Mice of individual groups were given diets as follows for 8 weeks similarly with Example 5.

Group 1: Normal diet (10 kcal % fat) only
Group 2: High-fat diet (60 kcal % fat) only
Group 3: Normal diet+flurbiprofen
Group 4: High-fat diet+flurbiprofen Flurbiprofen (F8514, produced by SIGMA) was diluted with drinking water so that the administration amount of flurbiprofen would be 10 mg/kg per day, and was orally administered to the mice in the form of drinking water.

Figure 11:
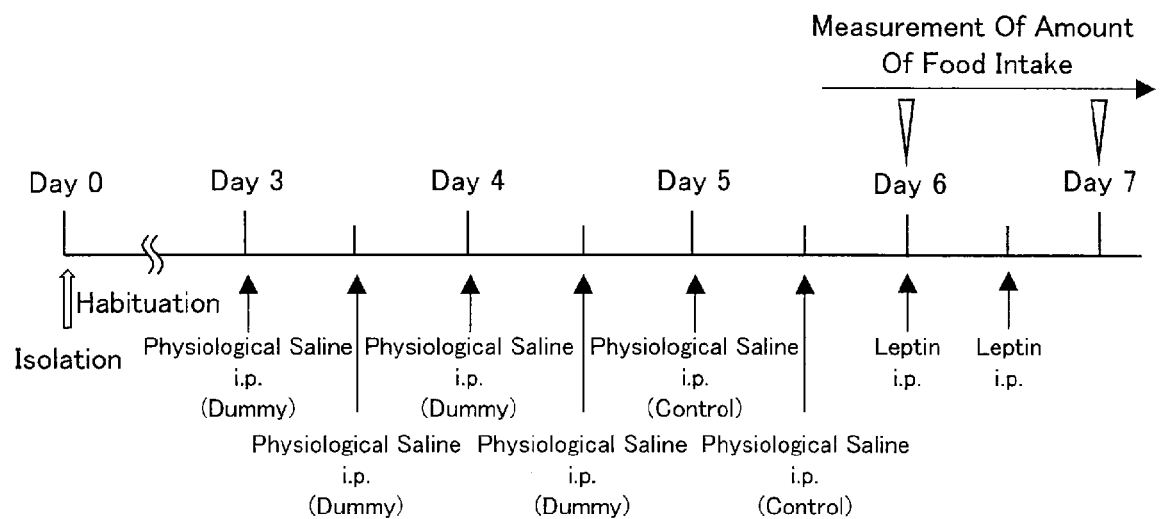
FIG. 11 is a drawing showing the procedure of the test in Example 7.

FIG. 11 is a drawing showing the procedure of the test in Example 7. As shown in FIG. 11, the mice raised for 8 weeks with high-fat diet or normal diet were isolated from one another so that there would be one mouse per cage. The mice were then habituated for 3 days. Day 0 was the date when the isolation started. In order to eliminate the influence of injection on feeding behavior, 5 mL/kg of physiological saline was intraperitoneally (i.p.) administered as dummy on Days 3 and 4. Further, 5 mL/kg of physiological saline was intraperitoneally (i.p.) administered on Day 5, and the amount of food intake up to 24 hours after the administration of physiological saline on Day 6 was regarded as a control.

Subsequently, 0.5 mg/kg of leptin (498-OB, rmLeptin, produced by R&D systems) was intraperitoneally (i.p.) administered on Day 6 and the amount of food intake up to 24 hours after the leptin administration was measured on Day 7. Using the ratio of the amount of food intake on Days 6 and 7 to the amount of food intake on Days 5 and 6 as a reference index, what influence leptin had on the amount of food intake (rate of change in amount of food intake) was analyzed. The rate of change in the amount of food intake is represented by formula (1) below.

$$\text{Rate of change in amount of food intake (\%)} = (\text{amount of food intake on Days 6 and 7/amount of food intake on Days 5 and 6}) \times 100 \quad (1)$$

Administrations of leptin and physiological saline were done twice per day at predetermined times (9:00 and 19:00).

Figure 12:
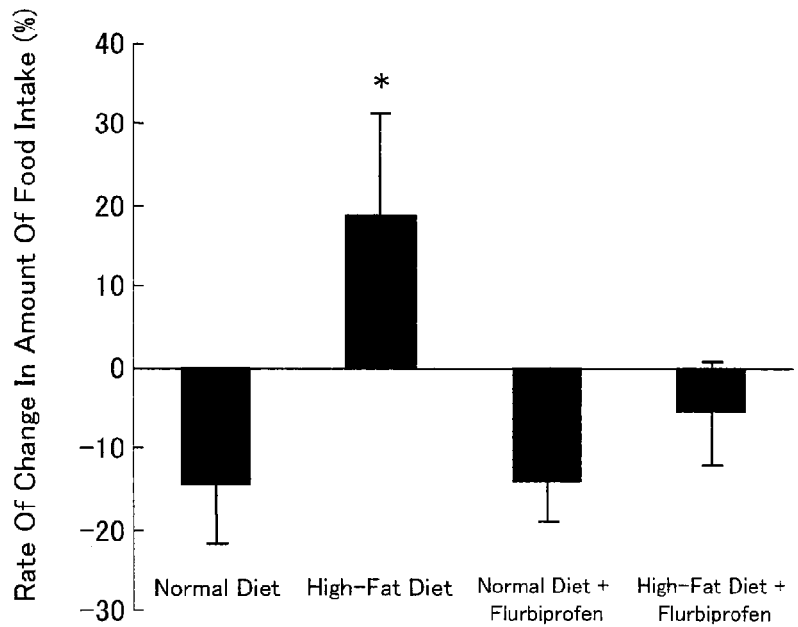
FIG. 12 is a graph showing changes in the amounts of food intake of mice of individual groups after leptin administration.

FIG. 12 shows the result. FIG. 12 is a graph showing changes in the amounts of food intake of the mice of individual groups after leptin administration. Values in the graph of FIG. 12 are averages of the rates (%) of changes in food intake of mice of each group (± their standard deviations) (n=6-8 with respect to each group). Further, statistic analysis was carried out using t-test. "*" in FIG. 12 indicates that there is a significant difference, with significance level of less than 5%, in the rate of change in the amount of food intake between the mice of Group 2 which had been given high-fat diet for 8 weeks and the mice of Group 1 which had been given normal diet.

As shown in FIG. 12, the mice of Group 2 which had been given high-fat diet for 8 weeks did not exhibit reduced food intake caused by leptin, and instead exhibited increased food intake. In contrast thereto, the mice of Group 4 which had been given high-fat diet with flurbiprofen for 8 weeks exhibited reduced food intake caused by leptin as a result of administration of flurbiprofen. There was no significant difference in the rate of change in the amount of food intake between the mice of Group 4 which had been given high-fat diet with flurbiprofen for 8 weeks and the mice of Group 1 which had been given normal diet. This indicates that there is no difference in the rate of change in the amount of food intake between the mice which had been given high-fat diet with flurbiprofen and the mice which had been given normal diet. Accordingly, it is considered that leptin resistance was prevented in the mice which had been given high-fat diet with flurbiprofen.

These results show that in the mice of Group 4, a leptin's signal functions normally, that is, in the mice of Group 4, flurbiprofen prevents leptin resistance caused by high-fat diet intake.

In view of the above, it is concluded that flurbiprofen is effective for preventing leptin resistance.

Example 8

Flurbiprofen Reduces Body Weight (Therapeutic Effect of Flurbiprofen)

In Example 8, effectiveness of flurbiprofen in ameliorating leptin resistance was confirmed by measuring a change in body weight of mice as a reference index. Specifically, 4 weeks-old male mice (C57BL/6 Cr Slc) had been given high-fat diet for 6 months so that leptin resistance would be induced in the mice. Thereafter, the mice were divided into two groups (each consisting of 14 mice), and the mice of individual groups were given the following diets for 3 weeks.
Control group (Cont): normal diet (10 kcal % fat) only
Flurbiprofen-administered group (Ful): normal diet+flurbiprofen Flurbiprofen (F8514, produced by SIGMA) was diluted with drinking water so that the administration amount of flurbiprofen would be 3 mg/kg per day, and was orally administered to the mice in the form of drinking water.

The rates of change in body weight of the mice of individual groups were measured with the date when administration of flurbiprofen started (0 week) as a reference. Further, the amount of visceral fat (g) was measured. The visceral fat was extracted from abdomens of the mice and wet weight thereof was measured.

Figure 13:
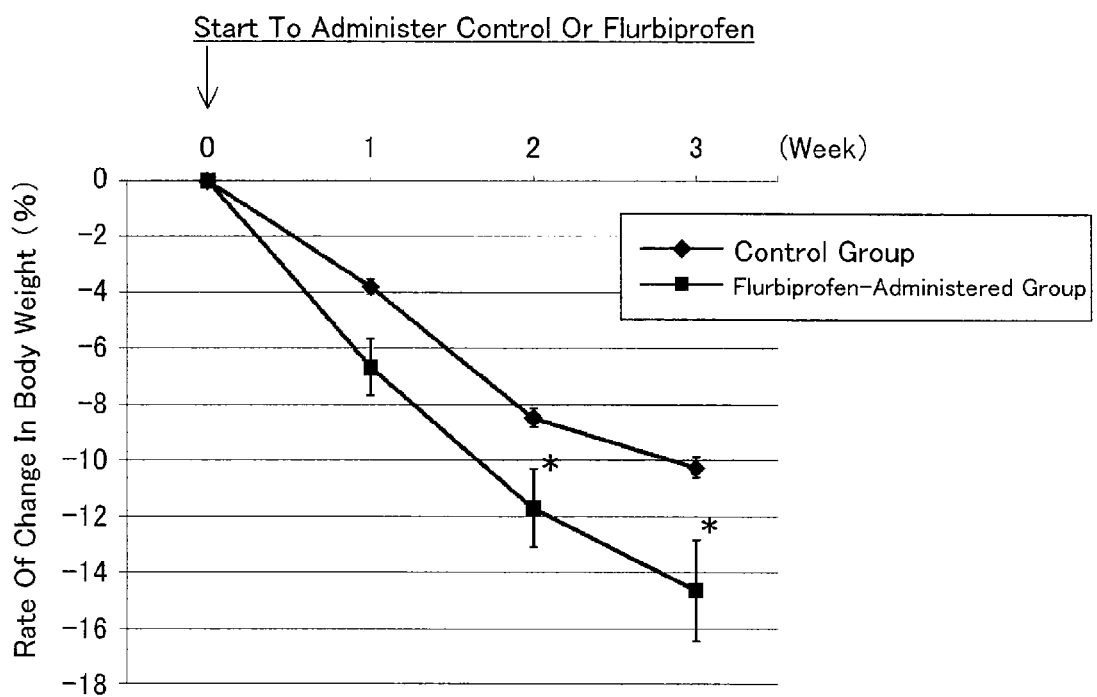
FIG. 13 is a graph showing the rates of change in body weights of mice of a control group and mice of a flurbiprofen-administered group.
Figure 14:
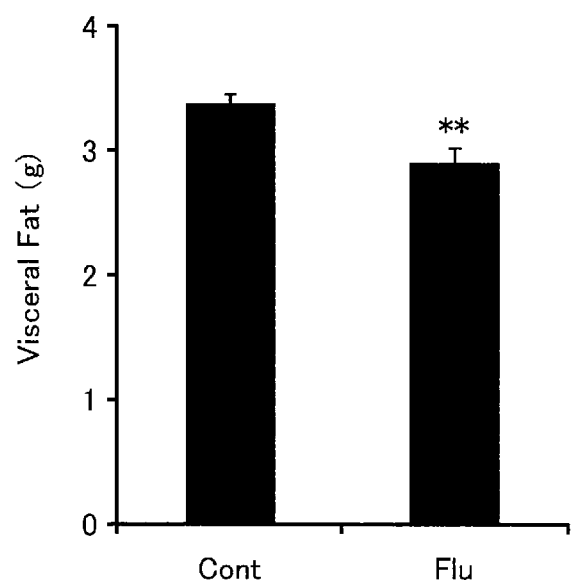
FIG. 14 is a graph showing the amounts of visceral fat of mice of a control group and mice of a flurbiprofen-administered group, which had been given normal diet for 3 weeks.

FIGS. 13 and 14 show the result. FIG. 13 is a graph showing the rates of change in body weight of the mice of the control group and the mice of the flurbiprofen-administered group. Values in the graph of FIG. 13 are averages of the rates (%) of change in body weight of mice of each group (± their standard deviations) (n=14 with respect to each group). Further, statistic analysis was carried out using t-test. "*" in FIG. 13 indicates that there is a significant difference, with significance level of less than 5%, in the rate of change in body weight between the mice of the control group and the mice of the flurbiprofen-administered group.

FIG. 14 is a graph showing the amount of visceral fat (g) of the mice of the control group and the mice of the flurbiprofen-administered group which had been given normal diet for 3 weeks. Values in the graph of FIG. 14 are averages of the amounts (g) of visceral fat of mice of each group (± their standard deviations) (n=14 with respect to each group). Further, statistic analysis was carried out using t-test. "**" in FIG. 14 indicates that there is a significant difference, with significance level of less than 1%, in the amount of visceral fat between the mice of the control group and the mice of the flurbiprofen-administered group.

As shown in FIG. 13, before flurbiprofen administration, the average body weight of the control group was 53.879±0.6299 g, and the average body weight of the flurbiprofen-administered group was 53.479±0.7804 g. On the other hand, 3 weeks after the administration of flurbiprofen, the average body weight of the control group was 48.371±0.6387 g, and the average body weight of the flurbiprofen-administered group was 45.543±1.1103 g. Thus, a significant decrease in body weight was observed (P<0.05). This result indicates that administration of flurbiprofen in the amount of clinical level (3 mg/kg per day) can ameliorate leptin resistance. Further, it was confirmed that the effect of ameliorating leptin resistance by flurbiprofen is observed 1 week after flurbiprofen administration.

Further, as shown in FIG. 14, it was confirmed that the amount of visceral fat of the mice of the flurbiprofen-administered group (3 weeks after flurbiprofen administration) was significantly decreased compared with the amount of visceral fat of the mice of the control group (P<0.01).

Example 9

Flurbiprofen Decreases Circulating Leptin Levels

Similarly with Example 8, 4 weeks-old male mice (C57BL/6 Cr Slc) had been given high-fat diet for 6 months so that leptin resistance would be induced in the mice. Thereafter, the mice were divided into two groups (each consisting of 8 mice), and the mice of individual groups were given the following diets for 3 weeks.
Control group (Cont): normal diet (10 kcal % fat) only
Flurbiprofen-administered group (Ful): normal diet+flurbiprofen Flurbiprofen (F8514, produced by SIGMA) was diluted with drinking water so that the administration amount of flurbiprofen would be 3 mg/kg per day, and was orally administered to the mice in the form of drinking water.

Figure 15:
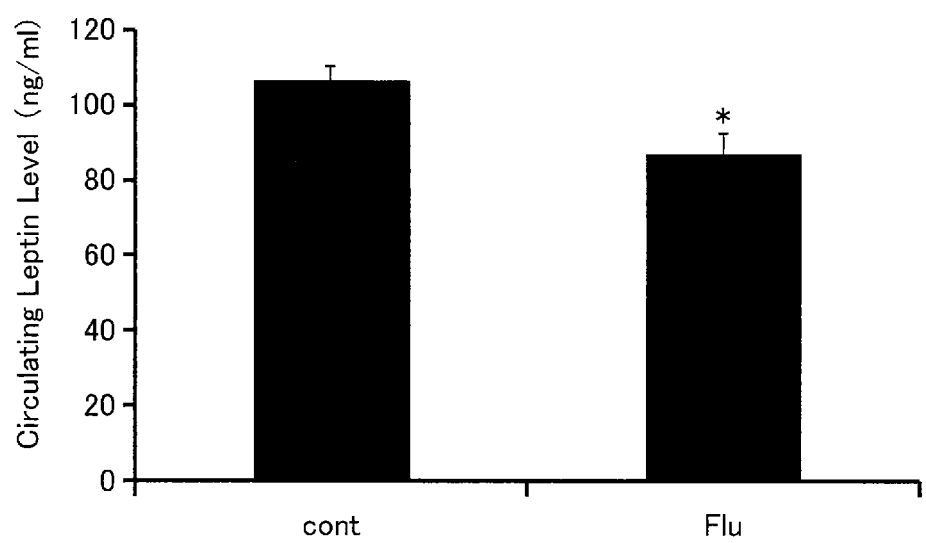
FIG. 15 is a graph showing circulating leptin levels of mice of a control group and mice of a flurbiprofen-administered group, which had been given normal diet for 3 weeks.

FIG. 15 shows the result of measurement of circulating leptin levels 3 weeks after flurbiprofen administration. FIG. 15 is a graph showing circulating leptin levels (ng/ml) of the mice of the control group and the mice of the flurbiprofen-administered group which had been given normal diet for 3 weeks. Values in the graph of FIG. 15 are averages of circulating leptin levels (ng/ml) of mice of each group (± their standard deviations) (n=8 with respect to each group). Further, statistic analysis was carried out using t-test. "*" in FIG. 15 indicates that there is a significant difference, with significance level of less than 5%, in circulating leptin levels between the mice of the control group and the mice of the flurbiprofen-administered group.

As shown in FIG. 15, circulating leptin level of the mice of the control group was 106.51±3.7122 (ng/ml). In contrast thereto, circulating leptin level of the mice of the flurbiprofen-administered group was 87.105±5.4415 (ng/ml). This confirmed that administration of flurbiprofen significantly decreases circulating leptin level (P<0.05).

In an individual in which leptin resistance is induced, leptin fails to function. To overcome this failure, the homeostatic regulatory system is operated. Activation of this system causes increased secretion of leptin in the blood stream. Consequently, the individual in which leptin resistance is induced has a higher leptin level in the blood stream. In contrast thereto, in a mouse of the flurbiprofen-administered group (Ful) to which flurbiprofen had been administered for 3 weeks, leptin resistance was ameliorated and the function of leptin was ameliorated, and so it was unnecessary to secrete more amount of leptin. Therefore, it is considered that the mice of the flurbiprofen-administered group (Ful) had significantly decreased circulating leptin levels compared with the mice of the control group (Cont). These results indicate that amelioration of leptin resistance by flurbiprofen can also be evaluated by measuring a decrease in circulating leptin levels.

Example 10

Change in Body Length by Administration of Flurbiprofen

Similarly with Example 8, 4 weeks-old male mice (C57BL/6 Cr Slc) had been given high-fat diet for 6 months so that leptin resistance would be induced in the mice. Thereafter, the mice were divided into two groups (each consisting of 8 mice), and the mice of individual groups were given the following diets for 3 weeks.

Control group (Cont): normal diet (10 kcal % fat) only
Flurbiprofen-administered group (Ful): normal diet+flurbiprofen Flurbiprofen (F8514, produced by SIGMA) was diluted with drinking water so that the administration amount of flurbiprofen would be 3 mg/kg per day, and was orally administered to the mice in the form of drinking water.

Figure 16:
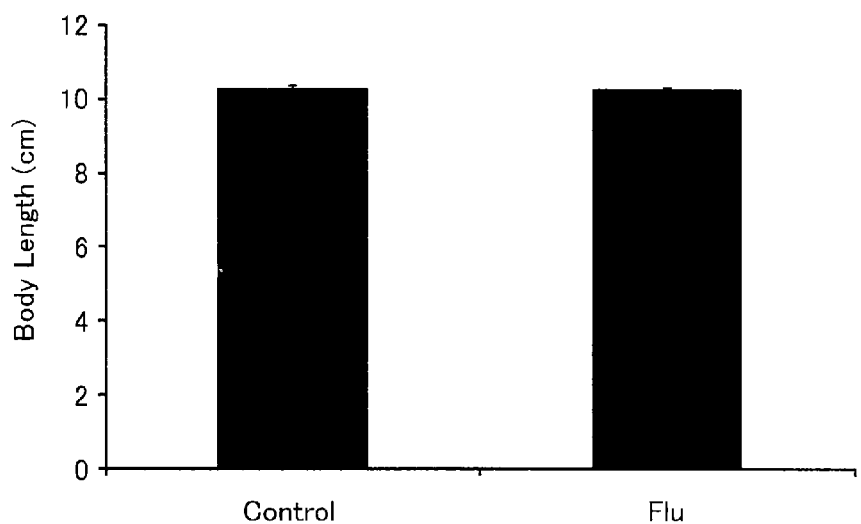
FIG. 16 is a graph showing the body length of mice of a control group and mice of a flurbiprofen-administered group, which had been given normal diet for 3 weeks.

The result of measurement of body length of the mice, to which flurbiprofen had been administered for 3 weeks, is shown in FIG. 16. FIG. 16 is a graph showing the body length (cm) of the mice of the control group and the mice of the flurbiprofen-administered group which had been given normal diet for 3 weeks. Values in the graph of FIG. 16 are averages of body lengths (cm) of mice of each group (± their standard deviations) (n=8 with respect to each group). Further, statistic analysis was carried out using t-test.

As shown in FIG. 16, there was no significant difference in body length between the mice of the control group and the mice of the flurbiprofen-administered group. This confirmed that the decrease in body weight of the mice in Example 8 was not caused in such a manner that administration of flurbiprofen induced toxicity or side-effect which blocked growth of the mice.

Example 11

Amelioration of Blood Glucose Level by Flurbiprofen

Similarly with Example 8, 4 weeks-old male mice (C57BL/6 Cr Slc) had been given high-fat diet for 6 months so that leptin resistance would be induced in the mice. Thereafter, the mice were divided into two groups (each consisting of 8 mice), and the mice of individual groups were given the following diets for 3 weeks.

Control group: normal diet (10 kcal % fat) only
Flurbiprofen-administered group: normal diet+flurbiprofen Flurbiprofen (F8514, produced by SIGMA) was diluted with drinking water so that the administration amount of flurbiprofen would be 3 mg/kg per day, and was orally administered to the mice in the form of drinking water.

The mice to which flurbiprofen had been administered for 3 weeks were subjected to a glucose tolerance test.

(Glucose Tolerance Test)

In Example 11, mice were fasted overnight for 17 hours from between 17:00 and 18:00 of the previous day, and fasted blood glucose level (pre) was measured by Freestyle freedom (NIPRO CORPORATION, blood glucose self-monitoring system) at 10:00 to 11:00. Thereafter, glucose was intraperitoneally (i.p.) administered so that the administration amount of glucose would be 2 g/kg. Blood glucose level was measured using Freestyle freedom (NIPRO CORPORATION, blood glucose self-monitoring system) 30 minutes, 1 hour, 2 hours, 3 hours, and 4 hours after glucose administration.

Figure 17:
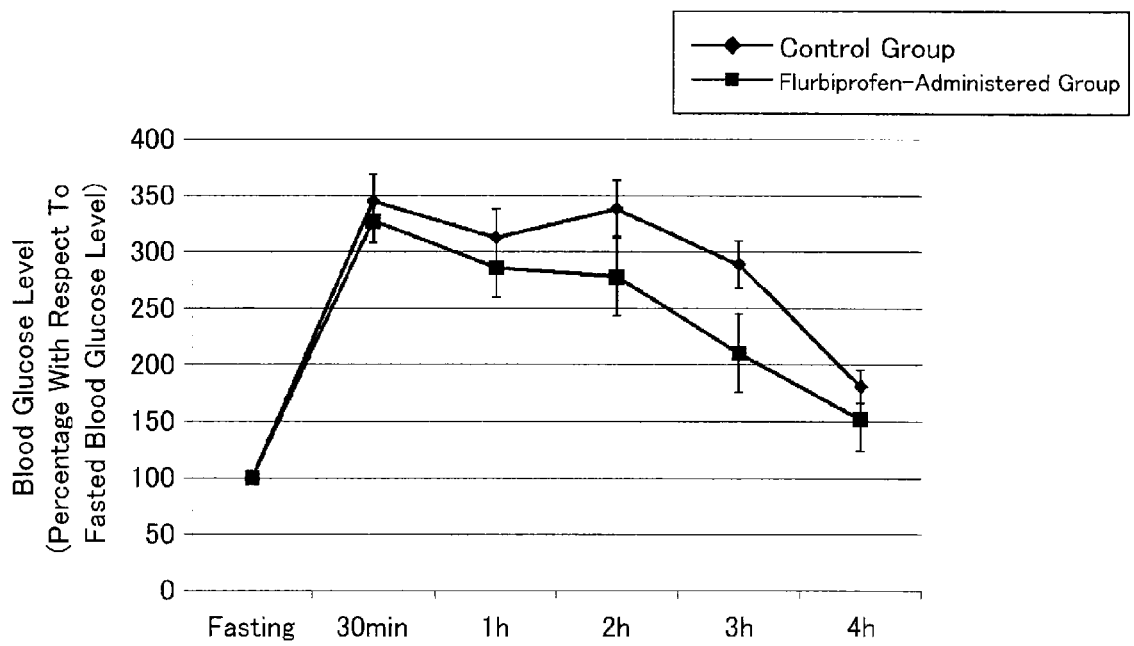
FIG. 17 is a graph showing the result of a glucose tolerance test.

The result of the measurement of blood glucose level is shown in FIG. 17. FIG. 17 is a graph showing the result of the glucose tolerance test. In FIG. 17, blood glucose levels at individual times after glucose administration are shown in percentages (%) with respect to fasted blood glucose level as 100%. Values in the graph of FIG. 17 are averages of blood glucose levels (%) of mice of each group (± their standard deviations) (n=8 with respect to each group). Further, statistic analysis was carried out using t-test.

As shown in FIG. 17, it was confirmed that blood glucose level of the mice of the flurbiprofen-administered group decreased 2 to 4 hours after glucose administration. In particular, it was confirmed that 3 hours after glucose administration, the mice of the flurbiprofen-administered group exhibited reduced blood glucose level compared with the mice of the control group ($P<0.07$ in t-test).

These results show that amelioration of leptin resistance by flurbiprofen can also be evaluated by measuring the change in blood glucose level by the glucose tolerance test.

In view of the above, it is concluded that flurbiprofen is effective for ameliorating leptin resistance.

Example 12

Influence of High-Fat Diet with Flurbiprofen on Amount of Mice Water Intake

In order to measure the amount of mice water intake, 4 weeks-old male mice (C57BL/6 Cr Slc) were divided into four groups (each consisting of 7-8 mice), were isolated from one another so that there would be one mouse per cage. The mice were then habituated for 2 days. The amount of mice water intake was measured every 24 hours for 4 days from the forenoon on the second day of the habituation, and the amount of mice water intake for 4 days was summed up.

Group 1: Normal diet (10 kcal % fat) only
Group 2: High-fat diet (60 kcal % fat) only
Group 3: Normal diet+flurbiprofen
Group 4: High-fat diet+flurbiprofen Flurbiprofen (F8514, produced by SIGMA) was diluted with drinking water so that the administration amount of flurbiprofen would be 10 mg/kg per day, and was orally administered to the mice in the form of drinking water.

Figure 18:
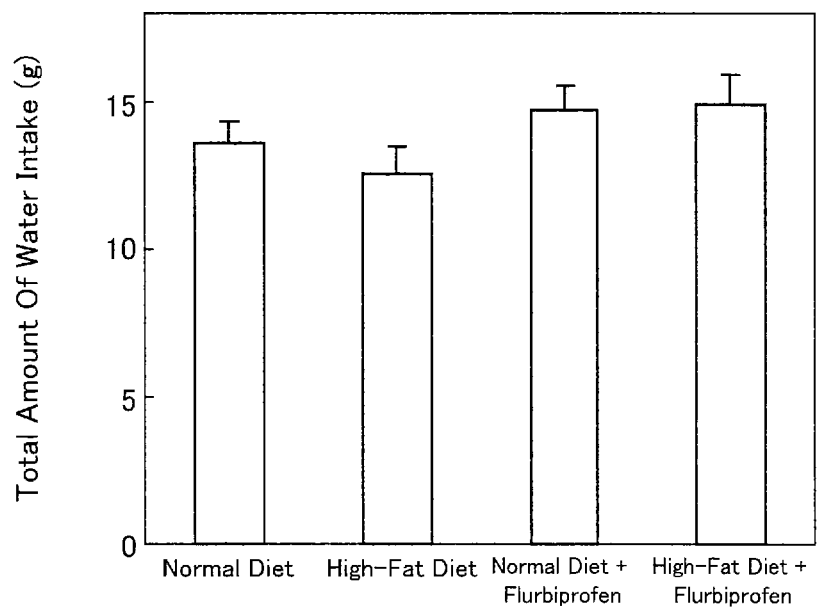
FIG. 18 is a graph showing the result of measurement of the amounts of mice water intake.

The result of measurement of the amount of mice water intake is shown in FIG. 18. FIG. 18 is a graph showing the result of the measurement of the amount of mice water intake. Values in the graph of FIG. 18 are averages of the total amounts (g) of water intake of mice of each group for 4 days (± their standard deviations) (n=7-8 with respect to each group). Further, statistic analysis was carried out using t-test.

The result of the measurement confirmed that the total of the amount of mice water intake for 4 days was constant regardless of whether flurbiprofen was administered or not, as shown in FIG. 18.

INDUSTRIAL APPLICABILITY

Use of the pharmaceutical composition of the present invention enables to ameliorate and/or prevent leptin resistance. Further, it is considered that use of the pharmaceutical composition of the present invention is effective for ameliorating and/or preventing diseases related to leptin resistance, such as diabetes, hypertension, hyperlipemia, and arteriosclerosis. Accordingly, the present invention is usable in the field of drugs and medicines.

The invention claimed is:

1. A method for ameliorating leptin resistance by administering, to a subject having leptin resistance, a pharmaceutical composition containing flurbiprofen.

2. The method as set forth in claim 1, wherein an administration amount of the flurbiprofen is 0.013-401 mg/kg per day for an adult.

* * * * *